(12) United States Patent
Eschborn et al.

(10) Patent No.: US 8,973,449 B2
(45) Date of Patent: Mar. 10, 2015

(54) DEVICE FOR AN ENDOSCOPE WASHING MACHINE

(75) Inventors: Sascha Eschborn, Ahrensburg (DE); Jens Waldmann, Hamburg (DE)

(73) Assignee: Olympus Winter & Ibe GmbH, Hamburg (DE)

( * ) Notice: Subject to any disclaimer, the term of this patent is extended or adjusted under 35 U.S.C. 154(b) by 608 days.

(21) Appl. No.: 13/141,504

(22) PCT Filed: Dec. 22, 2009

(86) PCT No.: PCT/EP2009/009223
§ 371 (c)(1),
(2), (4) Date: Aug. 25, 2011

(87) PCT Pub. No.: WO2010/075995
PCT Pub. Date: Jul. 8, 2010

(65) Prior Publication Data
US 2011/0296909 A1  Dec. 8, 2011

(30) Foreign Application Priority Data

Dec. 29, 2008  (DE) .......................... 10 2008 063 273

(51) Int. Cl.
*G01F 15/02*    (2006.01)
*A61B 19/00*    (2006.01)
*A61B 1/00*     (2006.01)
*A61B 1/12*     (2006.01)

(52) U.S. Cl.
CPC ............. *A61B 19/34* (2013.01); *A61B 1/00057* (2013.01); *A61B 1/123* (2013.01); *A61B 1/125* (2013.01); *A61B 2019/343* (2013.01); *A61B 2019/346* (2013.01)
USPC ............... 73/865.9; 73/49.2; 73/198

(58) Field of Classification Search
USPC ........................................ 73/49.2, 198, 865.9
See application file for complete search history.

(56) References Cited

U.S. PATENT DOCUMENTS

| 5,494,530 | A  | 2/1996 | Graf |
| 2003/0012688 | A1 | 1/2003 | Kippenhan |
| 2006/0047186 | A1 | 3/2006 | Annecke |

(Continued)

FOREIGN PATENT DOCUMENTS

DE   201 08 346 U 1     10/2001
DE   10 2004 040 734 B3  9/2005

(Continued)

OTHER PUBLICATIONS

"BeliMed Infection Control" brochure of BeliMed AG, Zug, Switzerland, which can be downloaded from www.belimed.com.

(Continued)

*Primary Examiner* — Randy W Gibson
*Assistant Examiner* — Natalie Huls
(74) *Attorney, Agent, or Firm* — Scully, Scott, Murphy & Presser, P.C.

(57) ABSTRACT

The invention relates to a test device for testing the inspection device of a washing machine for endoscopes, the inspection device including a connection that can be sealingly connected to an opening of an endoscope and feeding a fluid under pressure, said connector having a flow meter and/or a pressure transducer and the test device comprising at least one test chamber that can be sealingly connected to the connector by means of a test opening, wherein the test chamber is designed to be adjustable.

8 Claims, 2 Drawing Sheets

(56) References Cited

U.S. PATENT DOCUMENTS

| | | |
|---|---|---|
| 2007/0008160 A1* | 1/2007 | Nagai et al. .................... 340/610 |
| 2007/0100203 A1* | 5/2007 | Jackson et al. ................ 600/117 |
| 2009/0192354 A1* | 7/2009 | Hasegawa .................... 600/118 |
| 2013/0053635 A1* | 2/2013 | Yamane et al. ............... 600/103 |
| 2013/0233236 A1* | 9/2013 | Walta ............................ 116/201 |

FOREIGN PATENT DOCUMENTS

| | | |
|---|---|---|
| DE | 603 06 345 T2 | 6/2008 |
| EP | 0 709 056 A1 | 5/1996 |
| EP | 1 488 757 A1 | 12/2004 |
| EP | 1 779 769 A2 | 5/2007 |
| WO | WO 03/077960 A1 | 9/2003 |
| WO | WO 2008/019715 A1 | 2/2008 |

OTHER PUBLICATIONS

International Search Report dated Mar. 4, 2010 issued in PCT/EP2009/009223.

\* cited by examiner

DEVICE FOR AN ENDOSCOPE WASHING MACHINE

CROSS-REFERENCE TO RELATED APPLICATION

The present application is based upon and claims the benefit of priority from PCT/EP2009/009223 filed on Dec. 22, 2009, which claims benefit to DE 10 2008 063 273.2 filed on Dec. 29, 2008, the entire contents of each of which are incorporated herein by reference.

BACKGROUND

Field

The present invention generally relates to surgical endoscopes and washing machines for such surgical endoscopes, and particularly to a test device of the type indicated in claim 1.

Medical instruments and equipment that come into contact with the patient during operations are either purchased in sterile packs for single use or have to be cleaned and disinfected or sterilized after each use.

Flexible endoscopes pose a particular problem. Because of their high cost, they cannot be treated as disposable. What is more, they are sensitive to heat, chemicals and mechanical stresses and therefore have to be handled with care. Flexible endoscopes also have cavities and channels that require special treatment.

Therefore, in order to clean and disinfect flexible endoscopes, endoscope cleaning and disinfecting units, referred to below as "washing machines", have been developed, which are also distributed by the applicant. In washing machines of this type, endoscopes are treated from inside and out with cleaning and disinfecting fluids in successive stages. In the course of this, the endoscopes with access openings are connected to connections on the washing machine, from which fluid is supplied under pressure to the endoscope. The fluid, i.e. the cleaning or disinfecting fluid, is intended to flow through the endoscope. An adequate flow must be guaranteed for a certain period in order to achieve the desired cleaning and disinfecting effect.

The structurally long, thin channels in flexible endoscopes may become blocked during or after an operation, for example with coagulated blood or tissue residues. If a channel is blocked, it will not be flushed out and therefore not adequately sterilized.

In washing machines of this type, this is prevented by an inspection device, which in the case where a connection is connected to an endoscope, checks the flow and compares it, for example, with a theoretical value of an identical, clean endoscope. If the inspection device records a blockage, this will be displayed and the endoscope will have to be flushed for longer or, if necessary, pre-cleaned by hand and treated again by the washing machine.

The proper functioning of the inspection devices of such washing machines is of vital importance to the successful cleaning of the endoscopes. Therefore, the inspection devices have to be regularly checked.

Various test devices for washing machines are known from the state of the art.

DE 201 08 346 U1 shows a tube, which can be connected to the connection of a washing machine and in the test chamber of which test impurities have been placed. This allows the cleaning efficiency of the washing machine to be tested.

WO 2008/019715 A1 shows a dummy endoscope, which approximates largely to the external shape of a flexible endoscope and which can accommodate test impurities in test chambers and also on the outside, with which the cleaning efficiency can be checked.

Both these patents therefore show test devices, which can test only the cleaning efficiency but not the more important proper functioning of the inspection device.

The dummy endoscope shown in the second-named patent is also shown in the "BeliMed Infection Control" brochure of BeliMed AG, Zug, Switzerland, which can be downloaded from www.belimed.com. In the lower part of page 3, in the right column, a "seal adapter to simulate the blocking of a channel" is offered for this dummy endoscope. If a connection to a washing machine is blocked with this seal adapter, it can then be checked whether the washing machine inspection device correctly detects a blocked channel. This seal adapter therefore represents a generic test device.

The operation of this known test device is, however, very simple and does not allow it to be established whether the inspection device will really detect faults in a real endoscope.

SUMMARY

The task of the present invention therefore consists in creating a generic test device, which simulates the behaviour of real endoscopes.

According to the invention, the test chamber is developed to be adjustable. This makes it possible to adjust the test chamber to the desired parameters of a real endoscope. As when actually operating the washing machine, it is possible to simulate different endoscopes in succession and therefore obtain test results, which permit reliable conclusions to be drawn in respect of actual operation.

Inside, flexible endoscopes also comprise, in addition to through channels, which are flushed with fluid and checked, complex internal cavities, which are usually interconnected and in which sensitive equipment, e.g. electronics, optics and the like are arranged. These cavities lie between the channel walls and the outer walls of the endoscope and must be reliably sealed both in relation to the channels and to the outside. Therefore, washing machines comprise leak-detection devices, which apply excess or negative air pressure to the inside of the endoscope and measure the pressure gradient following shut-off, in order to determine the tightness. This washing machine leak testing device is also intended to be checked by the test device, as is also the case for example, in WO 2008/019715 A1. From preference, therefore, the invention, according to claim 2, provides in the test device a volume-adjustable leak test chamber, with which the washing machine leak testing device can be checked. The volume-adjustable design of the leak test chamber enables precise simulation of various real endoscopes.

From preference, according to claim 3, the leak test chamber is designed from connectable sub-chambers, so that the necessary volumes can be simulated using simple switching valves.

In order to simulate the channels of an endoscope, the test chamber is, from preference, designed as an adjustable test channel according to claim 4. This can, for example, be adjusted in respect of its length or patency in order to simulate real endoscopes.

From preference the test channel according to claim 5 is designed in the form of sub-channels that can be connected via switching valves. In this way, the complex channel systems of different endoscopes can be simulated as accurately as required, enabling the inspection device to be tested under very real conditions.

From preference, according to claim 6, the test channel is provided with at least one adjustable flow resistance. This allows the flow resistances of real endoscope channels to be precisely simulated, so that in complex channel systems, the hydraulic conditions can be exactly reproduced.

From preference, according to claim 7, a manometer is connected to the test chamber. The manometer can be used, for example, when checking the leak detection device, to check the manometer in the inspection device. However, the manometer may also be used for various other safety-relevant tests, for example, to check the pump pressure of the pump on the washing machine side as well as to check safety pressure sensors in the washing machine, which are intended to switch off in the event of dangerous excess pressures.

Preferably, according to claim 8, the test chamber can be connected via a flow meter. In this way, the flow meter is directly controlled in the connected connection of the washing machine inspection device.

The various connections of the washing machine for fluid and air must be connected to the corresponding openings in the endoscope. As the endoscope openings may be very different, according to type or manufacturer, inspection adapters are used, which comprise, for example, simple hoses with corresponding coupling pieces at their ends, and which in each case, fit at one end to a washing machine connection and at the other end to an opening in the endoscope. The test device according to the invention is intended to simulate different endoscopes and should therefore also be suited to an inspection adapter relevant to a particular endoscope. The test device must therefore simulate the corresponding connection openings when simulating an endoscope. From preference, this problem is solved according to claim 9 with a test adapter, which on the one hand fits the test openings of the test device and on the other, makes the openings of the simulated endoscope available.

From preference, the features of claim 10 are provided. In this way, from a table located in the control device, with said table containing the design data relevant to the endoscope being simulated, the test device can be set in such a way that this endoscope is precisely simulated. By switching over switching valves between the channels, channel branches may, for example, be simulated. By adjusting the flow resistance, the individual channels can be adapted to real channels. The volume of the inside of the endoscope can also be adjusted to check the leak detection device.

The test device should, as far as possible, simulate a real endoscope and should therefore also be positioned in place of an endoscope in the washing machine, for the test. However, the washing machine is closed, so that the test device can no longer be fitted with connection lines from the outside. From preference, therefore, according to claim 11, the test device has its own energy supply.

Data is obtained in the test device, e.g. for example, that relating to the manometer, according to claim 7 or to the flow meter according to claim 8. In the case of the test device positioned inside the closed washing machine, this data is not readily accessible. From preference therefore, according to claim 12, it is provided that the test device be designed to store or, if necessary, to transmit the data. The data obtained can therefore be stored in the test device until it is removed from the washing machine, or it is directly transmitted to the outside during operation, e.g. via suitable radio links.

BRIEF DESCRIPTION OF THE DRAWINGS

Examples of the invention are shown in diagram form in the drawings.

DETAILED DESCRIPTION

Figure 1:
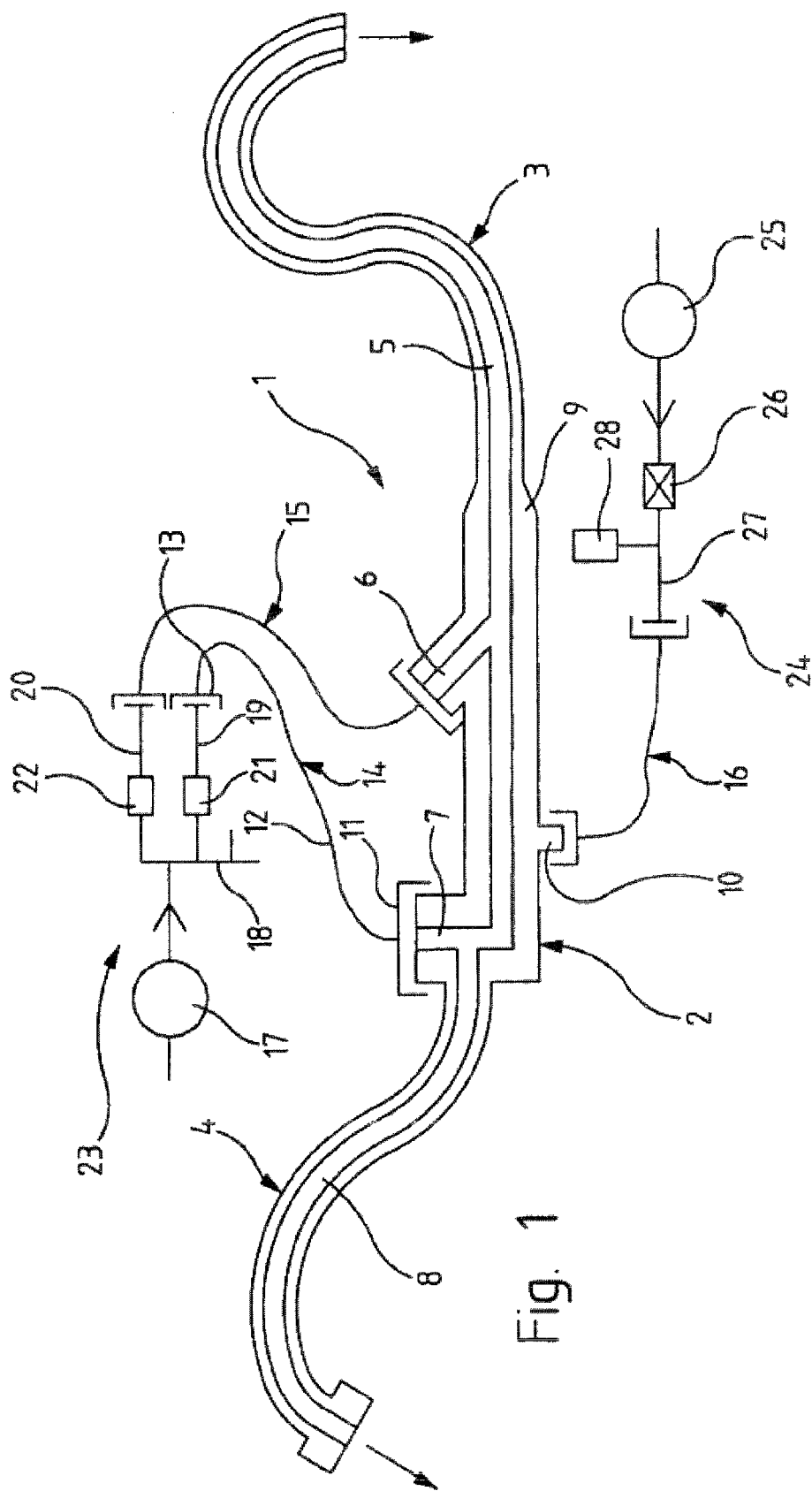
FIG. 1 shows a diagram of a simple, flexible endoscope with washing machine inspection device connected

FIG. 1 shows in highly diagrammatical form a flexible endoscope 1, where only the inner and outer walls are shown as a simple line. The endoscope 1 comprises a main body 2 from which an insertion hose 3 branches off, and which is intended to be inserted into the body, for example, into the intestine of a patient. A feed tube 4 also branches off from the main body 2. Inside the endoscope 1, a channel system is located with an insertion channel 5, which leads outwards from the distal tip of the insertion hose 3. The insertion channel 5 also passes through the main body 2. An access opening 6 is open to the outside and leads into the insertion channel. Biopsy forceps or other suitably long and flexible working instruments can be advanced through the access opening 6 into the insertion channel 5.

The insertion channel 5 ends at a valve opening 7, in which a control valve is normally positioned, which however is removed during cleaning. At the valve opening 7, a supply channel 8 branches off from the insertion channel 5 and continues to the end of the supply hose 4. Rinsing fluid, for example, is fed through the supply channel 8 and can be controlled by the valve which is normally positioned in the valve opening 7.

Around the channels 5 and 8, i.e. between them and the outer wall of the endoscope, an internal space 9 is developed, which must be well sealed both from the fluid carrying channels and towards the outside, because it receives sensitive instruments, not shown in FIG. 1, such as electronic or optical instruments. The internal space 9 is accessible from the outside through an opening 10. This opening is usually used to admit compressed air to the internal space 9 while the endoscope is in the washing machine, so that no water can penetrate as a result of leaks.

FIG. 1 shows the endoscope 1 illustrated in its connected state, as when it is being sterilised in a washing machine. The valve opening 7 is connected to a coupling piece 11 of a inspection adapter 14, said coupling piece 11 being adjusted to the valve opening. The inspection adapter comprises the coupling piece 14, a hose 12 and a coupling piece 13 at the other end of the hose.

A further inspection adapter 15 is connected to the access opening 6 by means of a suitable coupling piece. A third inspection adapter 16 is correspondingly connected to the opening 10 of the interior space 9. The coupling pieces of the inspection adapters on the endoscope side are suitably developed for the openings of the respective endoscope. The other coupling pieces fit the washing machine. If a different endoscope is connected, the set of inspection adapters must be changed as necessary.

The washing machine, which is not shown in greater detail, comprises a flushing pump 17, which pumps fluid, e.g. water or disinfectant in the direction of the arrow, into a distribution line 18, of which a first connection 19 is connected via a corresponding coupling to the inspection adapter 14. A parallel second connection 20 is connected to the inspection adapter 15. In other words, fluid can be pumped in parallel into the valve opening 7 and the access opening 6 of the endoscope 1. Located in the two connections 19 and 20 in each case is a flow meter, 21, 22. As indicated in the drawing by a branch, further connections with flow meters can branch off from the distribution line 18 and these further connections can be connected to other openings of more complex endoscopes.

The flow meters 21 and 22 are connected to an electronic device, not shown, in the washing machine, which knows the precise data relating to the connected endoscope 1, in particular its channel structure and flow resistances. The evaluation of the flow values measured by the flow meters 21, 22 therefore makes it possible to make statements about the patency of the channels 5 and 8 and also the patency of channel 5 in the area between the openings 6 and 7. Particularly a partially or completely blocked channel can be detected.

During the sterilisation process not only a channel inspection device 23 is connected, to which the first connection 19 and the second connection 20 belong, but also a leak inspection device 24, which is connected to the inspection adapter 16 and the interior space 9. This leak inspection device 24 supplies to the interior space 9 a fluid in gaseous form, normally air, and for this purpose, it has a gas pump 25, which pumps gas in the direction of the arrow through a switching valve 26 up to the coupling with the inspection adapter 16. A manometer 28 is connected between switching valve 26 and connection 27.

The leak inspection device 24 pressurises the internal space 9 of the endoscope and then locks the switching valve 26. The air pressure is then monitored by the manometer 28. The extent of any leak can be calculated from the pressure drop curve.

Figure 2:
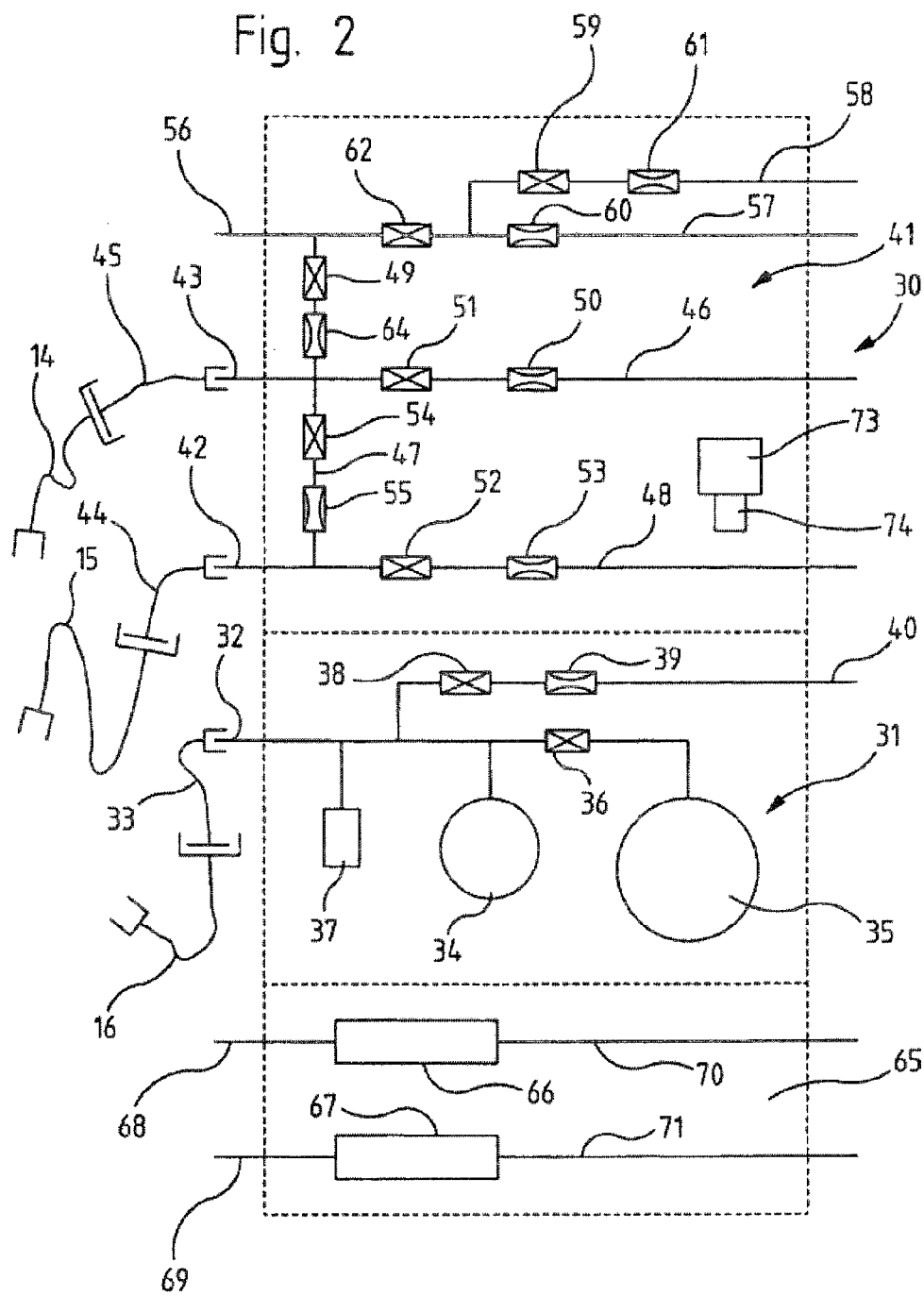
FIG. 2 shows the diagram of a test device according to the invention.

The test device 30 shown in FIG. 2 is used to check the washing machine inspection device comprising the parts 23 and 24 shown in FIG. 1.

The test device 30 in the embodiment shown comprises three compartments edged with broken lines, which may, for example, be positioned in a common housing and in each case have their own test devices. The housing is preferably watertight so that the test device 30 can be fitted inside a washing machine.

A leak testing device 31 comprises a test opening 32 shown in highly schematic form, which is to be connected to connection 27 of the leak inspection device 24. This connection is made via the inspection adapter 16, which does not, however, normally fit the test opening 32. Therefore an additional test adapter 33, which on the one hand fits the test device 30 shown in FIG. 2 and on the other, simulates the opening 10 of the endoscope 1, is provided between the test opening 32 and the inspection adapter 16.

The leak testing device 31 is intended to simulate the interior space 9 of the endoscope 1, but not only this but also interior spaces of other endoscopes. For this purpose the leak testing device 31 has a leak testing chamber comprising two chambers 34 and 35 of different size. The larger chamber 35 can be connected to the smaller chamber 34 by a switching valve 36. The chamber 34 is connected to the test opening 32. Also connected to the latter is a manometer 37, which is connected to a line 40, which leads to the outside through a switching valve 38 and an adjustable flow resistance 39. Both chambers 34 and 35 and, if necessary, other additional chambers of the leak testing device 31 can simulate random internal space sizes of endoscopes. By adjusting the flow resistance 39, random test leaks can be simulated and switched on and off using the switching valve 38. The manometer 28 provided directly on the washing machine side can be tested using the manometer 37.

A channel testing device 41 has two test openings 42 and 43, which, like test opening 32, can be appropriately connected by way of test adapters 44, 45 to the inspection adapters 14 and 15. With the latter they can be connected to the connections 19 and 20 of the channel inspection device 23. The test openings 42 and 43 must correspond to the access opening 6 or the valve opening 7, so that, for example, the endoscope 1 shown in FIG. 1 can be simulated.

The channel testing device 41 comprises a series of channels, with which larger channel systems of very complex endoscopes can also be simulated. Only some of the channels are required to simulate the endoscope 1 in FIG. 1.

In order to simulate endoscope 1 in FIG. 1, the test opening 43, which is connected to the inspection adapter 14, shall correspond to the valve opening 7. From there, a channel 46, which simulates the supply channel 8 of endoscope 1, runs to its free end with a drain that guarantees unimpeded drainage.

A cross-channel 47 runs to the test opening 42, which corresponds to the access opening 6 of the endoscope 1. The channel 47 thus corresponds to that part of the insertion channel 5, which lies inside the main body 2 of the endoscope 1, between openings 6 and 7.

From test opening 42, a channel 48 branches off, which likewise leads to a free discharge and which simulates that part of the insertion channel 5 of endoscope 1, which runs from the access opening 6 to the distal end of the insertion hose 3 of endoscope 1. No further parts of the channel system of the channel testing device 41 are needed to simulate the endoscope 1 illustrated in FIG. 1. For this purpose a switching valve 49 is closed.

In order to simulate the precise dimensions of the supply channel 8 of endoscope 1, its flow resistance is simulated by an adjustable flow resistance 50 in the channel 46. Channel 46 can be completely shut off using a switching valve 51 if, for example, it is not required when simulating another endoscope.

Appropriately, channel 48 is also adjustable and is fitted with a switching valve 52 and an adjustable flow resistance 53. The cross-channel 47 between the test openings 43 and 42 is likewise fitted with switching valve 54 and adjustable flow resistance 55 for the sake of completeness.

By adjusting the adjustable flow resistances 50, 53 and 55, the channel system of endoscope 1 can be precisely simulated. Channels can be completely shut-off by operating the switching valves. This is particularly necessary, if other endoscopes are simulated. Partial blockages may also be simulated by adjusting the adjustable flow resistances or complete blockages by closing the switching valves. The channel inspection device 23 of the washing machine must be monitored for corresponding reactions.

As already mentioned, channel testing device 41 can simulate not only endoscope 1 in FIG. 1 but also other endoscopes. If an additional test opening 56 is used with a channel 57, which leads to the outside, a correspondingly developed endoscope can be simulated. If a further channel 58 leading to the outside is provided in the endoscope parallel to channel 57, which leads to the outside, channel 58 can be connected or shut down using a switching valve 59. The flow resistances in channels 57 and 58 can be adjusted by adjustable flow resistances 60 and 61. If the switching valve 59 is operated, channel 58 is connected or shut down. The channel inspection device 23 should be able to detect this.

If an endoscope is to be simulated, which corresponds to that in FIG. 1, but has an additional opening, the test opening 56 is used and the channels 57 and 58 are shut down by a switching valve 62. The switching valve 49 is opened in order to establish the connection with the test openings 43 and 42, if necessary, by restricting the flow with an adjustable flow resistance 64.

The description of the channel testing device 41 in FIG. 2 is only intended as an example, to explain the possibilities of such a channel system. Actual test devices may comprise even more channels and valves, in order to be able to simulate very complex endoscopes.

In addition to the two compartments 31 and 41 discussed, the test device 30 also has a third compartment 65, which acts as a flow testing device. In the embodiment, it contains two flow meters 66 and 67, which are connected to test openings 68 and 69. At the other ends, the flow meters 66 and 67 are connected to the outside by the lines 70 and 71 shown.

The flow test device 65 can be connected, for example, using the test openings 68 and 69 and, if necessary, adapters to the connections 19 and 20 of the channel inspection device 23, so that fluid flows successively through the flow meters 22 and 66 or 21 and 67, thus making it possible to check directly the flow meters 22 and 21 on the washing machine side.

With appropriate wiring provided by additional adapters or by internal channel connections and valves, the flow meters 66 and 67 of the flow testing device 65 can also, for example, be switched between the test openings 42 and 43 of the channel testing device 41 and the adapters that branch off from it, so that when the channel testing device 41 is used, the flow measurement is simultaneously tested. The flow testing device 65 can, for example, only have one flow meter or even more than the two illustrated. Furthermore, additional manometers can also be provided in the flow testing device 65.

As shown in FIG. 2, a control device 73 is fitted at a suitable place in the test device 30 and is connected by control lines, not shown, to the switching valves shown and the adjustable flow resistances of the test device 30, in order to set the latter by way of appropriate control signals. The control device 73 can preferably obtain information from a built-in memory, where the data from different endoscopes is stored. If, for example, the endoscope shown in FIG. 1 is called up from this memory, the control device 73 of the test device 30 shown in FIG. 2 will close the switching valve 49 and open the switching valve 54, as well as the switching valves 51 and 52. The adjustable flow resistances 50, 53 and 55 would be set to the values of endoscope 1. The control device 73 can, of course, also control the leak testing device 31.

Additional electronic devices can be provided, which are built into the test device 73 or developed as separate instruments.

Data, for example, measurements from the manometer 37 and the flow meters 66 and 67 is collected in the test device 30. The switching and control states of all switching valves and flow resistances can also be stored for logging. For this purpose, an internal memory can be provided, which stores all the measured values until the test process is concluded and the test device 30 can be removed from the washing machine in order to connect it by a suitable data interface to a computer from where the data can be called off.

A data transmission device can also be provided, which regularly transmits the data obtained from the washing machine, for example, using suitable wireless transmission methods.

As the test device 30 has to operate for a longish time inside a washing machine, a cable connection would be unsuitable. This applies not only to the data transfer but also to the power supply. For this reason a battery 74, shown in FIG. 2, is provided, with which the control device 73 as well as the switching valves and adjustable flow resistances can be supplied.

The invention claimed is:

1. A test device for testing an inspection device of a washing machine for washing at least a first type of endoscope and a second type of endoscope,
wherein the first type of endoscope has:
a first internal space having a first sealed volume, and
a first channel having a first flow resistance,
wherein the second type of endoscope has:
a second internal space having a second sealed volume different from the first sealed volume, and
a second channel having a second flow resistance different from the first flow resistance,
wherein the inspection device comprises:
a leak inspection portion comprising:
a gas pump configured to be selectively attached to the first internal space and the second internal space, and to pump gas into the first internal space and the second internal space to thereby pressurize the first internal space and the second internal space; and
an inspection device-side pressure sensor configured to detect a pressure in the first internal space and a pressure in the second internal space; and
a channel inspection portion comprising:
a flushing pump configured to be selectively attached to the first channel and the second channel, and to pump fluid through the first channel and the second channel, and
an inspection device-side flow resistance sensor configured to detect a flow resistance of the first channel and a flow resistance of the second channel,
wherein the test device comprises:
a leak testing portion configured to be detachably attachable to the leak inspection portion of the inspection device to be in fluid communication with the leak inspection portion, the leak testing portion comprising:
a plurality of testing chambers, wherein each of the plurality of testing chambers has a testing chamber volume; and
one or more leak testing portion valve configured to changeably connect different combinations of the testing chamber volumes of the plurality of testing chambers to simulate:
the first sealed volume of the first internal space of the first type of endoscope; and
the second sealed volume of the second internal space of the second type of endoscope; and
a channel testing portion configured to be detachably attachable to the channel inspection portion of the inspection device to be in fluid communication with the channel inspection portion, the channel testing portion comprising:
a test channel; and
one or more adjustable flow resistance configured to changeably adjust a flow resistance of the test channel to simulate:
the first flow resistance of the first channel of the first type of endoscope; and
the second flow resistance of the second channel of the second type of endoscope.

2. The test device according to claim 1, wherein the leak testing portion further comprises:
a test line in communication with one or more of the plurality of testing chambers;
one or more adjustable flow resistance configured to changeably adjust a flow resistance of the test line to simulate a test leak in the one or more of the plurality of testing chambers;
a leak testing portion-side pressure sensor configured to detect a pressure in the test line.

3. The test device according to claim 2, further comprising a memory for storing the pressure detected by the leak testing portion-side pressure sensor.

4. The test device according to claim 1, wherein the channel testing portion further comprises a channel testing portion-side flow resistance sensor configured to detect a flow resistance of the test channel.

5. The test device according to claim 4, further comprising a memory for storing the flow resistance detected by the channel testing portion-side flow resistance sensor.

6. The test device according to claim 1,
wherein the leak testing portion is configured to be detachably attachable through one or more leak inspection adapter to the leak inspection portion of the inspection device, and
wherein the channel testing portion is configured to be detachably attachable through one or more channel inspection adapter to the channel inspection portion of the inspection device.

7. The test device according to claim 1, further comprising:
a memory configured to store information regarding one or more of the first sealed volume, the second sealed volume, the first flow resistance, and the second flow resistance; and
a control device configured to control the leak testing portion and the channel testing portion based on the information stored in the memory.

8. The test device according to claim 1, further comprising an energy supply for powering the leak testing portion and the channel testing portion.

* * * * *